(12) United States Patent
Chen et al.

(10) Patent No.: US 11,529,153 B2
(45) Date of Patent: Dec. 20, 2022

(54) VACCINE GENERATION

(71) Applicants: University of Washington, Seattle, WA (US); Seattle Children's Hospital, Seattle, WA (US)

(72) Inventors: James Chen, Seattle, WA (US); Tanner Clark, Seattle, WA (US); Thomas Lendvay, Seattle, WA (US)

(73) Assignees: UNIVERSITY OF WASHINGTON, Seattle, WA (US); Seattle Children's Hospital, Seattle, WA (US)

( * ) Notice: Subject to any disclaimer, the term of this patent is extended or adjusted under 35 U.S.C. 154(b) by 0 days.

(21) Appl. No.: 17/244,610

(22) Filed: Apr. 29, 2021

(65) Prior Publication Data
US 2022/0054149 A1 Feb. 24, 2022

Related U.S. Application Data

(60) Provisional application No. 63/068,729, filed on Aug. 21, 2020.

(51) Int. Cl.
*A61B 17/20* (2006.01)
*A61M 5/31* (2006.01)
(Continued)

(52) U.S. Cl.
CPC ............ *A61B 17/20* (2013.01); *A61K 9/0021* (2013.01); *A61K 39/215* (2013.01);
(Continued)

(58) Field of Classification Search
CPC ...... A61K 2039/5152; A61K 2039/521; A61K 2039/5252; A61K 39/00; A61K 39/0011;
(Continued)

(56) References Cited

U.S. PATENT DOCUMENTS 3,817,389 A 6/1974 Weichselbaum
4,395,789 A 8/1983 Bruce
(Continued)

FOREIGN PATENT DOCUMENTS

CA 2276023 C 4/2002
CA 2473924 A1 7/2003
(Continued)

OTHER PUBLICATIONS

Almeida, A., et al. "Phage Therapy and Photodynamic Therapy: Low Environmental Impact Approaches to Inactivate Microorganisms in Fish Farming Plants," Marine Drugs 7(3): pp. 268-313, Jun. 30, 2009.

(Continued)

*Primary Examiner* — Brandy S Lee
(74) *Attorney, Agent, or Firm* — Christensen O'Connor Johnson Kindness PLLC

(57) ABSTRACT

An apparatus for vaccine generation includes a syringe with a cavity that includes a solution with photosensitizers. Microbial particles are added to the solution. A light source is capable of emitting one or more wavebands of light that are effectively absorbed by the one photosensitizers to generate singlet oxygen in the solution and other radical species that rapidly react with and damage lipids, proteins, DNA, and RNA of the microbial particles. This damage produces immunogens that can be applied as a vaccine to viruses and other infectious microbial particles. A plunger that fits within a proximal opening in the syringe is used for forcing the solution including the immunogens through the filter and out of the syringe while the photosensitizers, debris and unwanted microbial particles are trapped within the filter.

20 Claims, 2 Drawing Sheets

(51) Int. Cl.
  *A61M 5/32*    (2006.01)
  *A61K 9/00*    (2006.01)
  *A61K 39/215*  (2006.01)
  *B01L 3/02*    (2006.01)
  *A61K 41/00*   (2020.01)
  *A61B 10/00*   (2006.01)
  *A61K 39/00*   (2006.01)

(52) U.S. Cl.
  CPC ....... *A61K 41/0057* (2013.01); *A61M 5/3145* (2013.01); *A61M 5/3293* (2013.01); *B01L 3/02* (2013.01); *A61B 10/0045* (2013.01); *A61K 2039/54* (2013.01); *A61M 2202/30* (2013.01); *A61M 2205/7509* (2013.01); *A61M 2209/04* (2013.01); *B01L 2300/0681* (2013.01)

(58) Field of Classification Search
  CPC .... A61K 39/12; A61K 39/21; A61K 41/0019; A61K 2039/54; A61K 39/215; A61K 41/0057; A61K 9/0021; A61B 10/0045; A61B 17/20; A61M 2202/30; A61M 2205/7509; A61M 2209/04; A61M 5/3145; A61M 5/3293
  See application file for complete search history.

(56) References Cited

U.S. PATENT DOCUMENTS

| | | | |
|---|---|---|---|
| 4,402,318 A | 9/1983 | Swartz | |
| 5,445,608 A | 8/1995 | Chen et al. | |
| 5,715,837 A | 2/1998 | Chen | |
| 5,741,316 A | 4/1998 | Chen et al. | |
| 5,766,234 A | 6/1998 | Chen et al. | |
| 5,782,896 A | 7/1998 | Chen et al. | |
| 5,814,008 A | 9/1998 | Chen et al. | |
| 5,827,186 A | 10/1998 | Chen et al. | |
| 5,830,526 A | 11/1998 | Wilson et al. | |
| 5,865,840 A | 2/1999 | Chen | |
| 5,997,569 A | 12/1999 | Chen et al. | |
| 6,080,160 A | 6/2000 | Chen et al. | |
| 6,096,066 A | 8/2000 | Chen et al. | |
| 6,210,425 B1 | 4/2001 | Chen | |
| 6,238,426 B1 | 5/2001 | Chen | |
| 6,273,904 B1 | 8/2001 | Chen et al. | |
| 6,281,611 B1 | 8/2001 | Chen et al. | |
| 6,319,273 B1 | 11/2001 | Chen et al. | |
| 6,331,744 B1 | 12/2001 | Chen et al. | |
| 6,344,050 B1 | 2/2002 | Chen | |
| 6,416,531 B2 | 7/2002 | Chen | |
| 6,454,789 B1 | 9/2002 | Chen et al. | |
| 6,520,669 B1 | 2/2003 | Chen et al. | |
| 6,580,228 B1 | 6/2003 | Chen et al. | |
| 7,018,395 B2 | 3/2006 | Chen | |
| 7,288,106 B2 | 10/2007 | Heacock et al. | |
| 7,320,786 B2 | 1/2008 | Chen | |
| 7,511,031 B2 | 3/2009 | Chen | |
| 7,802,572 B2 | 9/2010 | Hahne | |
| 8,057,464 B2 | 11/2011 | Chen et al. | |
| 8,226,946 B2 | 7/2012 | Chen | |
| 8,450,359 B2 | 5/2013 | McCoy et al. | |
| 8,685,005 B2 | 4/2014 | Dahm et al. | |
| 8,685,071 B2 | 4/2014 | Burwell et al. | |
| 8,759,092 B2 | 6/2014 | Goodrich | |
| 9,149,651 B2 | 10/2015 | Keltner et al. | |
| 9,278,148 B2 | 3/2016 | Fewkes et al. | |
| 9,527,918 B2 | 12/2016 | Fiori et al. | |
| 10,307,610 B2 | 6/2019 | Keltner et al. | |
| 2003/0114434 A1 | 6/2003 | Chen et al. | |
| 2006/0223729 A1 | 10/2006 | Hamblin et al. | |
| 2007/0038204 A1 | 2/2007 | Chen et al. | |
| 2007/0059316 A1 | 3/2007 | Pallenberg et al. | |
| 2007/0059791 A1 | 3/2007 | Goodrich | |
| 2007/0129776 A1 | 6/2007 | Robins et al. | |
| 2007/0133935 A1 | 6/2007 | Fine | |
| 2007/0142880 A1 | 6/2007 | Barnard et al. | |
| 2007/0286878 A1 | 12/2007 | Harruna | |
| 2008/0015189 A1 | 1/2008 | Hamblin et al. | |
| 2008/0107636 A1 | 5/2008 | Goodrich | |
| 2009/0317436 A1 | 12/2009 | Wilson et al. | |
| 2010/0241054 A1 | 9/2010 | Dacey, Jr. et al. | |
| 2010/0274330 A1 | 10/2010 | Burwell et al. | |
| 2010/0305436 A1 | 12/2010 | Chen et al. | |
| 2011/0008372 A1 | 1/2011 | Chen | |
| 2011/0009464 A1 | 1/2011 | Chen | |
| 2011/0014239 A1* | 1/2011 | Goodrich ............... | A61K 39/12 424/277.1 |
| 2011/0110818 A1 | 5/2011 | Mowbray-d'Arbela et al. | |
| 2012/0100039 A1 | 4/2012 | Appeaning et al. | |
| 2012/0209359 A1 | 8/2012 | Chen et al. | |
| 2014/0052050 A1 | 2/2014 | Courtin | |
| 2014/0303547 A1 | 10/2014 | Loupis et al. | |
| 2016/0091399 A1* | 3/2016 | Chen ................... | A61M 5/3145 73/863.23 |
| 2016/0193338 A1 | 7/2016 | Loupis et al. | |
| 2016/0220728 A1 | 8/2016 | Adams et al. | |
| 2016/0270895 A1 | 9/2016 | Zoll | |
| 2017/0056603 A1* | 3/2017 | Cowan ................. | A61M 5/365 |
| 2018/0099063 A1 | 4/2018 | Lyons et al. | |
| 2018/0243790 A1 | 8/2018 | Grossman | |
| 2019/0161562 A1 | 5/2019 | Bakar et al. | |
| 2019/0314502 A1 | 10/2019 | Wei et al. | |
| 2020/0315280 A1 | 10/2020 | Kaye | |

FOREIGN PATENT DOCUMENTS

| | | |
|---|---|---|
| CA | 2537235 A1 | 1/2005 |
| CN | 104589717 B | 3/2017 |
| CN | 208597758 U | 3/2019 |
| EP | 1644082 A2 | 4/2006 |
| EP | 1684865 A1 | 8/2006 |
| WO | 98/32494 A1 | 7/1998 |
| WO | 1999/49823 A1 | 10/1999 |
| WO | 2004/108249 A1 | 12/2004 |
| WO | WO2005/032459 A2 | 4/2005 |
| WO | 2006086770 A2 | 8/2006 |
| WO | 2008046019 A1 | 4/2008 |
| WO | 2014/130740 A1 | 8/2014 |
| WO | 2018/022926 A1 | 2/2018 |
| WO | 2019/183320 A1 | 9/2019 |

OTHER PUBLICATIONS

Hasenleitner, M., et al. "In the Right Light: Photodynamic Inactivation of Microorganisms Using a LED-Based Illumination Device Tailored for the Antimicrobial Application," Antibiotics 9(1): pp. 1-13, Dec. 30, 2019.
Trempolec, N., et al. "Photodynamic Therapy-Based Dendritic Cell Vaccination Suited to Treat Peritoneal Mesothelioma," Cancers 12(3): pp. 1-16, Feb. 27, 2020.
Weaver, E.A. "Dose Effects of Recombinant Adenovirus Immunization in Rodents," Vaccines 7(4):144 pp. 1-11, Oct. 10, 2019.
Hankaniemi, M.M., et al. "A comparative study of the effect of UV and formalin inactivation on the stability and immunogenicity of a coxsackievirus B1 vaccine," Vaccine 37: pp. 5962-5971, Aug. 27, 2019.
Mills, D., et al. "Ultraviolet germicidal irradiation of influenza-contaminated N95 filtering facepiece respirators," AJIC: American Journal of Infection Control 46(7): pp. e49-e55, 2018.
Bull, J.J., et al. "Transmissible Viral Vaccines," Trends in Microbiology 26(1): pp. 6-15, Jan. 2018.
Barrett, P.N., et al. "Vero cell technology for rapid development of inactivated whole virus vaccines for emerging viral diseases," Expert Review of Vaccines 16(9): pp. 883-894, Jul. 17, 2017.
Klasse, P.J. "Molecular determinants of the ratio of inert to infectious virus particles," Progress in Molecular Biology and Translational Science 129: pp. 285-326, 2015.
Klausberger, M. et al. "One-shot vaccination with an insect cell-derived low-dose influenza A H7 virus-like particle preparation protects mice against H7N9 challenge," Vaccine 32(3): pp. 355-362, Nov. 18, 2013.

(56) References Cited

OTHER PUBLICATIONS

Mertes, P., et al. "Methylene blue-treated plasma: an increased allergy risk?" The Journal of Allergy and Clinical Immunology 130(3): pp. 808-812, Jun. 2, 2012.
Seghatchian, J. et al. "Main properties of the THERAFLEX MB-plasma system for pathogen reduction," Transfusion Medicine and Hemotherapy 38(1): pp. 55-64, Jan. 27, 2011.
Marcus, P. et al. "In vitro analysis of virus particle subpopulations in candidate live-attenuated influenza vaccines distinguishes effective from ineffective vaccines," Journal of Virology 84(21): pp. 10974-10981, Aug. 13, 2010.
Quan, F. et al. "Dose sparing enabled by skin immunization with influenza virus-like particle vaccine using microneedles," Journal of Controlled Release 147(3): pp. 326-332, Aug. 6, 2010.
Victoria, J. et al. "Viral nucleic acids in live-attenuated vaccines: Detection of minority variants and an adventitious virus," Journal of Virology 84(12): pp. 6033-6040, Mar. 25, 2010.
Maves, R. et al. "Immunogenicity of a psoralen-inactivated dengue virus type 1 vaccine candidate in mice." Clinical and Vaccine Immunology 17(2): pp. 304-306, Feb. 2010.
Prausnitz, M.R., et al. "Microneedle-based vaccines," Current Topics in Microbiology and Immunology 333: pp. 369-393, Jul. 15, 2010.
Geeraedts, F., et al. "Superior immunogenicity of inactivated whole virus H5N1 influenza vaccine is primarily controlled by toll-like receptor signalling," PLoS Pathogens 4(8): p. e1000138, Aug. 29, 2008.
Monath, T.P. et al. "A live, attenuated recombinant west nile virus vaccine," Proceedings of the National Academy of Sciences, USA 103(17): pp. 6694-6699, Mar. 9, 2006.
Meurice, F. et al. "Immunogenicity and safety of a live attenuated varicella vaccine (oka/SB bio) in healthy children," The Journal of Infectious Diseases 174(Supplement 3): pp. S324-S329, Nov. 1996.
THERAFLEX-MB Plasma-Processing Principle, advertisement published by MacoPharma, Sep. 2007.
"Influenza Vaccine," Cytiva, https://www.gelifesciences.com/en/us/solutions/bioprocessing/knowledge-center/influenza-vaccine-manufacturing [retrieved Mar. 30, 2020], 10 pages.
Borkar, T.G., et al. "Techniques Employed in Production of Traditional Vaccines Commonly Used by Military Forces: A Review," Journal of Archives in Military Medicine 7(102):e96149, pp. 1-12, Jun. 2019.
Plotino, G., et al. "Photodynamic therapy in endodontics," International Endodontic Journal (52): pp. 760-774, 2019.
Meller, D., et al. "Photodisinfection Therapy: Essential Technology for Infection Control," <https://infectioncontrol.tips/2020/01/17/photodisinfection-therapy/> [retrieved Jul. 30, 2020], 20 pages.
Boyce, J.M., "Modern technologies for improving cleaning and disinfection of environmental surfaces in hospitals," © 2016 <https://www.ncbi.nlm.nih.gov/pmc/articles/PMC4827199/> [retrieved Jul. 30, 2020], 20 pages.
"What is Photodisinfection?," Ondine Biomedical, <https://ondinebio.com/technology> [retrieved Aug. 12, 2020], 5 pages.
Henneberry, B. How Surgical Masks are Made. Thomas Industry. <https://www.thomasnet.com/articles/other/how-surgical-masks-are-made/>[Accessed Mar. 21, 2020], 1 page.
Clear Polypropylene. Omnexus: The material selection platform. <https://omnexus.specialchem.com/centers/clear-polypropylene> [Accessed Mar. 21, 2020], 1 page.
Midden, R.W., Wang, S.Y., "Singlet Oxygen Generation for Solution Kinetics: Clean and Simple," Journal of the American Chemical Society, 105(13):4129-4135, Jun. 29, 1983.
Naito, K. et al. "Single-molecule detection of airborne singlet oxygen," Journal of the American Chemical Society 128(51): pp. 16430-16431, 2006.
Ogilby, P.R. "Singlet oxygen: There is indeed something new under the sun," Chemical Society reviews 39(8): pp. 3181-3209, 2010.

Zhao, Y. et al. "Singlet oxygen generation on porous superhydrophobic surfaces: Effect of gas flow and sensitizer wetting on trapping efficiency," The Journal of Physical Chemistry A 118(45): pp. 10364-10371, 2014.
Gao, R. et al. "Nano-photosensitizer based on layered double hydroxide and isophthalic acid for singlet oxygenation and photodynamic therapy," Nature communications 9(1):2798, pp. 1-10, 2018.
Felgentrager, A., et al. "Singlet oxygen generation in porphyrin-doped polymeric surface coating enables antimicrobial effects on *Staphylococcus aureus*," Physical Chemistry Chemical Physics:PCCP, 16(38): pp. 20598-20607, 2014.
Pushalkar, S. et al. "Superhydrophobic photosensitizers: Airborne 1O2 killing of an in vitro oral biofilm at the plastron interface," ACS Applied Materials & Interfaces 10(30): pp. 25819-25829, Jul. 4, 2018.
Hwang, J. et al. "Study of singlet oxygen dynamics on silicon polymer matrix," Journal of Analytical Methods in Chemistry vol. 2019 Article ID 2584686, pp. 1-6, Feb. 19, 2019.
Bartusik, D. et al. "Bacterial inactivation by a singlet oxygen bubbler: Identifying factors controlling the toxicity of 1O2 bubbles," Environmental Science & Technology 46(21): pp. 12098-12104, Oct. 18, 2012.
Aebisher, D. el al. "Superhydrophobic surfaces as a source of airborne singlet oxygen through free space for photodynamic therapy," ACS Applied Bio Materials 3(4): pp. 2370-2377, Mar. 17, 2020.
Dancer, Stephanie J. "Controlling hospital-acquired infection: focus on the role of the environment and new technologies for decontamination." Clinical microbiology reviews 27.4 (2014): 665-690.
Pyrek, K. "Portable medical equipment: A significant source of transmission," Feb. 1, 2018, 16 pages.
Russotto, V., Cortegiani, A., Raineri, S. M., & Giarratano, A. Bacterial contamination of inanimate surfaces and equipment in the intensive care unit. Journal of Intensive Care. 2015;3(1):54, pp. 1-8.
Gabriele Messina, Emma Ceriale, Daniele Lenzi, Sandra Burgassi, Elena Azzolini, Pietro Manzi. Environmental contaminants in hospital settings and progress in disinfecting techniques. BioMed research international. 2013;2013:429780, 8 pages.
Bonetta S, Bonetta S, Motta F, Strini A, Carraro E. Photocatalytic bacterial inactivation by TiO2-coated surfaces. AMB Expr. 2013;3(1):1-8. https://www.ncbi.nlm.nih.gov/pubmed/24090112. doi: 10.1186/2191-0855-3-59.
Air permeable(breathable) film, <http://tamstech.net> [Accessed Mar. 25, 2020], 1 page.
Siracusa, Valentina. "Food packaging permeability behaviour: A report." International Journal of Polymer Science 2012 (2012), 2 pages.
Makdoumi K, Hedin M, Bäckman A. Different photodynamic effects of blue light with and without riboflavin on methicillin-resistant *Staphylococcus aureus* (MRSA) and human keratinocytes in vitro. Lasers Med Sci. 2019;34(9):1799-1805.
Kino, K., et al. Commentary on the phototoxicity and absorption of vitamin B2 and its degradation product, lumichrome. Pharmaceutica analytica acta. 2015;6(8). doi: 10.4172/2153-2435.1000403.
Koshi E, Mohan A, Rajesh S, Philip K. Antimicrobial photodynamic therapy: An overview. Journal of Indian Society of Periodontology. 2011;15(4):323-327, 1 page.
Bhat M, Acharya S, Prasad K, Kulkarni R, Bhat A, Bhat D. Effectiveness of erythrosine-mediated photodynamic antimicrobial chemotherapy on dental plaque aerobic microorganisms: A randomized controlled trial. Journal of Indian Society of Periodontology. 2017;21(3):210-215.
Lee Y, Park H, Lee J, Seo H, Lee S. The photodynamic therapy on *Streptococcus* mutans biofilms using erythrosine and dental halogen curing unit. International journal of oral science. 2012;4(4):196-201.
Fracalossi C, Nagata JY, Pellosi DS, et al. Singlet oxygen production by combining erythrosine and halogen light for photodynamic inactivation of *Streptococcus* mutans. Photodiagnosis and Photodynamic Therapy. 2016;15:127-132. https://search.datacite.org/works/10.1016/j.pdpdt.2016.06.011. doi: 10.1016/j.pdpdt.2016.06.011, 1 page.

(56) References Cited

OTHER PUBLICATIONS

Wood S, Metcalf D, Devine D, Robinson C. Erythrosine is a potential photosensitizer for the photodynamic therapy of oral plaque biofilms. Journal of antimicrobial chemotherapy. 2006;57(4):680-684.

Gahleitner, Markus, et al. Sterilization effects on polypropylene: technology and polymer type effects., Jan. 2003 , <https://www.researchgate.net/publication/288596501>, 3 pages.

"Cover Picture: Optik & Photonik Apr. 2015," Abstract, vol. 10, Issue 4, 2015,<https://doi.org/10.1002/opph.201590064>, 2 pages.

Molitch-Hou, M., "First 3D Printed Fiber Optics Created by University of Sydney researchers with Desktop 3d Printer," 2015, 3D Printing Industry, The Authority on Additive Manufacturing, <https://3dprintingindustry.com/news/first-3d-printed-fiber-optics-createdby-university-of-sydney-researchers-with-desktop-3d-printer-55047/> [Accessed Mar. 24, 2020], 1 page.

Ismail, Salim, et al. "Efficacy of a novel light-activated antimicrobial coating for disinfecting hospital surfaces." Infection Control & Hospital Epidemiology 32.11 (2011): 1130-1132.

Lee, Im-Soon, et al. "Aerosol particle size distribution and genetic characteristics of aerosolized influenza A H1N1 virus vaccine particles." Aerosol and Air Quality Research 11.3 (2011): 230-237.

Meyer, Michelle, et al. "Aerosolized Ebola vaccine protects primates and elicits lung-resident T cell responses." The Journal of clinical investigation 125.8 (2015): 3241-3255.
Noimark, Sacha, et al. "Incorporation of methylene blue and nanogold into polyvinyl chloride catheters; a new approach for light-activated disinfection of surfaces." Journal of Materials Chemistry. 2012; 22(30): 15388-15396. <https://doi.org/10.1039/C2JM31987J>, 1 page.
Noimark, Sacha, Elaine Allan, and Ivan P. Parkin. "Light-activated antimicrobial surfaces with enhanced efficacy induced by a dark-activated mechanism." Chemical Science 5.6 (2014): 2216-2223.
Piccirillo, Clara, et al. "Antimicrobial activity of methylene blue and toluidine blue O covalently bound to a modified silicone polymer surface." Journal of Materials Chemistry 19.34 (2009): 6167-6171.
Fecht, S., "The First Fully 3-D Printed LEDs Are Here," 2014, <https://www.popsci.com/article/technology/first-fully-3-d-printed-leds-are-here/> [Accessed Mar. 24, 2020], 8 pages.
Waldman, Robert H., John J. Mann, and Parker A. Small. "Immunization against influenza: prevention of illness in man by aerosolized inactivated vaccine." Jama 207.3 (1969): 520-524. doi:10.1001/jama. 1969.03150160032007, 1 page.
Chen, James, et al., "Disinfection Method and Apparatus," U.S. Appl. No. 17/405,900, filed Aug. 18, 2021, 55pages.
Chen, James, et al., "Antimicrobial Preventive Netting," U.S. Appl. No. 17/244,688, filed Apr. 29, 2021, 35 pages.
Chen, James, et al., "Photosensitizer Combination," U.S. Appl. No. 17/463,245, filed Aug. 31, 2021, 46 pages.
Chen, James, et al., "Invisible Singlet Film," U.S. Appl. No. 17/389,936, filed Jul. 30, 2021, 33 pages.
International Search Report and Written Opinion dated Feb. 2, 2022, issued in International Application No. PCT/US2021/046419, filed Aug. 18, 2021, 11 pages.
International Search Report and Written Opinion dated Feb. 1, 2022, issued in International Application No. PCT/US2021/048444, filed Aug. 31, 2021, 14 pages.
International Search Report and Written Opinion dated Nov. 30, 2021, in International Application PCT/US2021/0046417, filed Aug. 18, 2021, 11 pages.
International Search Report and Written Opinion mailed Dec. 6, 2021, in International Application PCT/JS2021/046722, filed Aug. 19, 2021, 9 pages.
International Search Report and Written Opinion dated Nov. 8, 2021, issued in International Application No. PCT/US2021/046416, filed Aug. 18, 2021, 9 pages.
International Search Report and Written Opinion dated Dec. 6, 2021, in International Application PCT/US2021/046722, filed Aug. 19, 2021, 9 pages.

* cited by examiner

VACCINE GENERATION

CROSS-REFERENCE TO RELATED APPLICATION

This application claims the benefit of U.S. Provisional Application No. 63/068,729, filed on Aug. 21, 2020, herein expressly incorporated by reference in its entirety.

BACKGROUND

Generation of viral and bacterial vaccines is a time consuming, resource intensive, and complex process performed in dedicated manufacturing facilities. To manufacture an influenza vaccine for example, a sample of a particular type of influenza virus derived from candidate vaccine virus stock is first grown in eggs or in cell culture. Then, the particular type of virus is inactivated, and immunogens such as antigens are released in some methodologies. A number of means of viral inactivation have been developed including use of formaldehyde, beta-propiolactone, or application of gamma radiation. Then, the immunogens are purified using a number of separation steps. Adjuvants to enhance the recipient immune response and stabilizers to enhance shelf life are part of the vaccine production process after purification. Then, a vaccine solution can be placed into a vial and refrigerated or frozen prior to vaccination. In a low resource setting such as in the developing world, the costs, facilities, availability of trained personnel, and expertise are not readily available, and vaccine pharmaceutical manufacturing largely is in the hands of a relatively small number of major companies. In the case of influenza vaccines, intermittent decisions must be made in advance of each flu season by coordinated governmental agencies such as the Centers for Disease Control and Prevention (CDC), World Health Organization, and the US Food and Drug Administration, as to what viral type composition hopefully best matches what will potentially infect the population at risk. The influenza vaccine may or may not be a good match during flu season, and reduced effectiveness due to mismatch can occur, for example, during the 2004-2005 flu season, effectiveness was estimated to be very low at 10% by the CDC. Cost, problems with availability, war and civil unrest, difficult logistics, and other factors impede the uptake and use of Influenza vaccines in low resource settings.

Clearly there is a need for apparatuses and methods that increase the availability and use of vaccines such as the influenza vaccine in low resource settings, that are low cost, do not require refrigeration or freezing, are developed to be effective against regional and local viral types, and that do not require a major manufacturing plant.

SUMMARY

According to embodiments of this disclosure, methods and apparatus for producing vaccines are disclosed. In one embodiment, swabs are used to obtain microbial samples from the nose, mouth, and throat, and/or collection in specimen containers of samples of sputum, mucus, saliva, urine, diarrhea, tears, sweat, blood, semen, vaginal secretions, and the like, in particular any fluid or available body fluid or substance containing viruses or other microbial particles in sufficient quantity to generate an effective vaccine. The collected microbial particles are then transferred into a container, vessel, or syringe, which contains a solution of one or more photosensitizers, which when exposed to at least one light source, generates singlet oxygen in the solution which inactivates the microbial particles, producing immunogens which can be used as a vaccine. The vaccine is purified by filtering the photodynamically treated solution and then the ultrafiltrate is injected subcutaneously, intravenously, and/or applied topically to the skin or mucosa, such as in the mouth or nose.

In one embodiment, the availability and use of vaccines such as the influenza vaccine in low resource settings can be increased. The vaccines according to the disclosure can be low cost, not requiring refrigeration or freezing, and can be developed to be effective against regional and local viral types. In particular, different types of vaccines according to the disclosure do not require a major manufacturing plant or refrigeration.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Example devices, methods, and systems are described herein. It should be understood the words "example," "exemplary," and "illustrative" are used herein to mean "serving as an example, instance, or illustration." Any embodiment or feature described herein as being an "example," being "exemplary," or being "illustrative" is not necessarily to be construed as preferred or advantageous over other embodiments or features. The example embodiments described herein are not meant to be limiting. It will be readily understood that aspects of the present disclosure, as generally described herein, and illustrated in the figures, can be arranged, substituted, combined, separated, and designed in a wide variety of different configurations, all of which are explicitly contemplated herein.

Furthermore, the particular arrangements shown in the Figures should not be viewed as limiting. It should be understood other embodiments may include more or less of each element shown in a given Figure. Further, some of the illustrated elements may be combined or omitted. Yet further, an example embodiment may include elements not illustrated in the Figures. As used herein, with respect to any measurements "about" means+/−5%.

It shall be understood that the term "microbial", as used herein refers to an infectious microorganism, pathogen, or agent, including one or more of a virus, viroid, bacterium, archaea, protists, protozoan, prion, fungus, or the like.

Further, it shall be understood that the term "immunogen", as used herein refers to an antigen or any other substance that induces both an immune response by a patient's immune system and generation of antibodies that bind to the immunogen.

The current disclosure details apparatus and methods of use based on photodynamic therapy, which is a combination of one or more photosensitizers that when activated by particular wavelengths of light leads to the generation of singlet oxygen and other radical species that rapidly react with and damage lipids, proteins, DNA, and RNA of microbial particles. The damage to these biological constituents can generate immunogens when applied to viruses and other infectious microbial particles.

Figure 1:
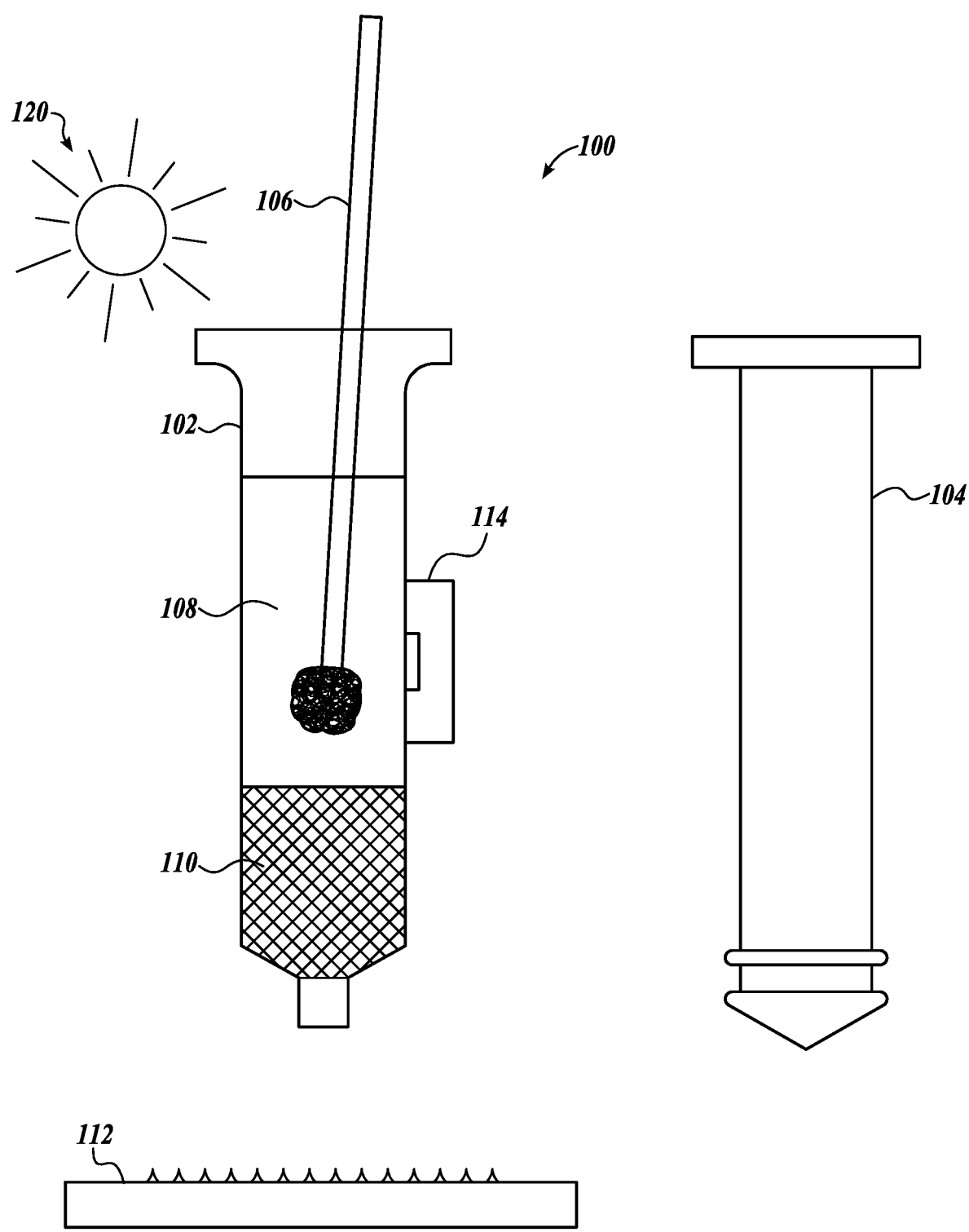
FIG. 1 is a diagrammatical illustration of an apparatus for generating a vaccine and administering the vaccine.

FIG. 1 is a diagrammatical illustration of an apparatus 100 for creating vaccines. In one embodiment, a cavity of a syringe 102 can be used as a container. The cavity of the syringe 102 is filled with a solution ranging in volume from 0.1 ml to 20 ml, for example, and containing one or more photosensitizers. A photosensitizer is a compound that can generate at least singlet oxygen in response to light provided at particular wavebands or wavelengths. Singlet oxygen is known by the chemical formula, $^1O_2$. Photosensitizers can include, but are not limited to, all types of methylene blue derivatives and methylene blue itself, chlorophyll derivatives, tetrapyrrole structures, porphyrins, chlorins, bacteriochlorins, phthalocyanines, texaphyrins, prodrugs such as aminolevulinic acids, phenothiaziniums, squaraine, boron compounds, various transition metal complexes, hypericin, riboflavin, curcumin, psoralens, tetracyclines, flavins such as riboflavin, titanium dioxide, photosensitizer nanocompositions, and combinations. A photosensitizer can be in the form of a powder to which a biocompatible solution such as saline is added, or be supplied in a liquid form, for example, as an aqueous solution, or pre-loaded into the syringe, container, or vessel.

In one embodiment, the photosensitizer concentration can range from 0.0001 micromolar to 5,000 micromolar. In one embodiment, a preferred photosensitizer concentration can range from 0.001 to 1000.0 micromolar. In one embodiment, a more preferable range of photosensitizer concentration is from 10.0 micromolar to 100.0 micromolar.

In one embodiment, a swab 106 is used to collect a viral sample from the mouth, nose, or nasopharynx. The swab 106 is then placed into the cavity of the syringe 102, with the plunger removed, and which may be preloaded, or added later, with one or more photosensitizers in a solution 108. The swab 106 is swirled in the photosensitizer solution 108 which releases the microbial particles into the photosensitizer solution 108. The swab 106 can then be removed.

Then, the syringe 102 is exposed to light which photoactivates the photosensitizer to generate singlet oxygen which inactivates the microbial particles in the solution, producing immunogens which can be used as a vaccine. In one embodiment, the syringe 102 or another container is made from a transparent or translucent material such as plastic, polymer, or glass. In one embodiment, a light source 114 can include one or more LEDs which are incorporated into the syringe wall which may be made of a transparent or translucent material. Although not shown, the light source 114 may be located inside the cavity of the syringe, or external to the walls of the syringe.

In one embodiment, ambient light or sunlight can also be used as the photoactivating light in place of an artificial light. Any light source can be used that emits the particular wavebands or wavelengths of light that are effectively absorbed by the one or more photosensitizers leading to singlet oxygen generation in a solution. The light source 114 can be comprised of one or more light emitting diodes (LED), xenon lamps, fluorescent bulbs and tubes, incandescent light bulbs, electroluminescent devices, lasers, ambient light, or natural sunlight, and the like. Other known or contemplated light sources are not excluded, and include all known wavelengths and wavebands known to lead to a photodynamic effect particular to the one or more photosensitizing agents.

In one embodiment, the exposure time can range from 1 second to 2 hours, and the lux (lumen per square meter) can range from 10 to 50,000. In one embodiment, a preferred exposure time is from 1 minute to 1 hour and a lux range from 100 to 10,000. In one embodiment, the most preferred exposure time is from 5 minutes to 30 minutes, and a lux range from 100 to 10,000.

After light exposure of the one or more photosensitizers in the solution in the cavity of the syringe for a period of time long enough to generate singlet oxygen that causes inactivation of the microbial particles and generation of immunogens, the syringe plunger 104 is positioned at the proximal syringe opening and depressed forcing the inactivated microbial photosensitizer solution 108 through a filter 110 which may include one or more filters. As shown, filter 110 may be located at the end of the cavity inside syringe 102. Although not shown, filter 110 may be disposed at one or more internal portions of the cavity, or outside the distal end of syringe at an external outlet. The filter 110 is selected to be inert in the photosensitizer solution. In one embodiment, the filter 110 is sized to allow immunogens to pass while trapping larger debris and unwanted microbial particles. The size of particles the filter 110 can trap will be dependent on the particular microbial particles and immunogens that are desired to pass through the filter. Most viruses can range in diameter from 5 nanometers to 300 nanometers, though some giant viruses can be measured in the 0.4 micron range. Different virus families generally have diameter and size ranges, that allow the filter type and design to be selected such that the viral type to be treated is efficiently captured, if the virus particle is intact, while allowing immunogens such as immunogenic viral fragments and antigens to pass through. Filters of varying types and pore sizes are available commercially, for example, a MF-MILLIPORE® membrane from Merck which can have a 0.22 μm pore size, and which would be expected to capture intact viruses 0.3 μm in diameter or larger. Other factors such as an electrical charge on the filter can lead to improved trapping of microbial particles as well. The SARS-CoV-2 virus has a diameter of approximately 0.1 μm, and can be trapped by standard polypropylene filter material found in N95 respirators which could be utilized, as an example, to trap intact virions while allowing smaller fragments, such as immunogens, through after treatment.

In one embodiment, the filter 110 has a pore size from 0.1 μm to 1.0 μm. In one embodiment, the filter 110 has a pore size from 0.1 μm to 0.5 μm. In one embodiment, the filter 110 has a pore size from 0.1 μm to 0.3 μm. In some embodiments, the pore size can be smaller than 0.1 μm. In some embodiments, the size of the immunogens is known, and the pore size of the filter 110 is selected to allow the immunogens to pass while trapping debris and unwanted microbial particles.

In one embodiment, the filter 110 can be placed in a separate vessel outside the syringe 102 which can then be attached and detached to the outlet opening of the syringe 102. In one embodiment, a second filter 116 is provided at the end of the syringe 102 to remove the one or more photosensitizers. The second filter 116 can be provided within the syringe 102 or as a separable filter attached to the outlet of the syringe 102. A suitable filter 110 is known by the name MILLIPORE®. A suitable second filter 116 to remove methylene blue is known under the name BLUE-FLEX™ MB.

In one embodiment, after filtering, the photosensitizer solution which includes the immunogens can be deposited onto a microneedle array 112, which is used as a vaccine delivery vehicle.

In one embodiment, immunologic adjuvants such as aluminum salts, squalene, saponins, Freund's adjuvant, monophosphoryl lipid A, AS04, Endocine™, or other known or contemplated vaccine adjuvants, can be applied to the oral and/or nasal mucosa, or administered subcutaneously, intramuscularly, or by other routes, which can increase the immunogenic response.

In one embodiment, the filtered solution of immunogens is applied to a microneedle patch 112 and administered, and then the microneedle patch 112 is used to deliver the vaccine intradermally.

Figure 2:
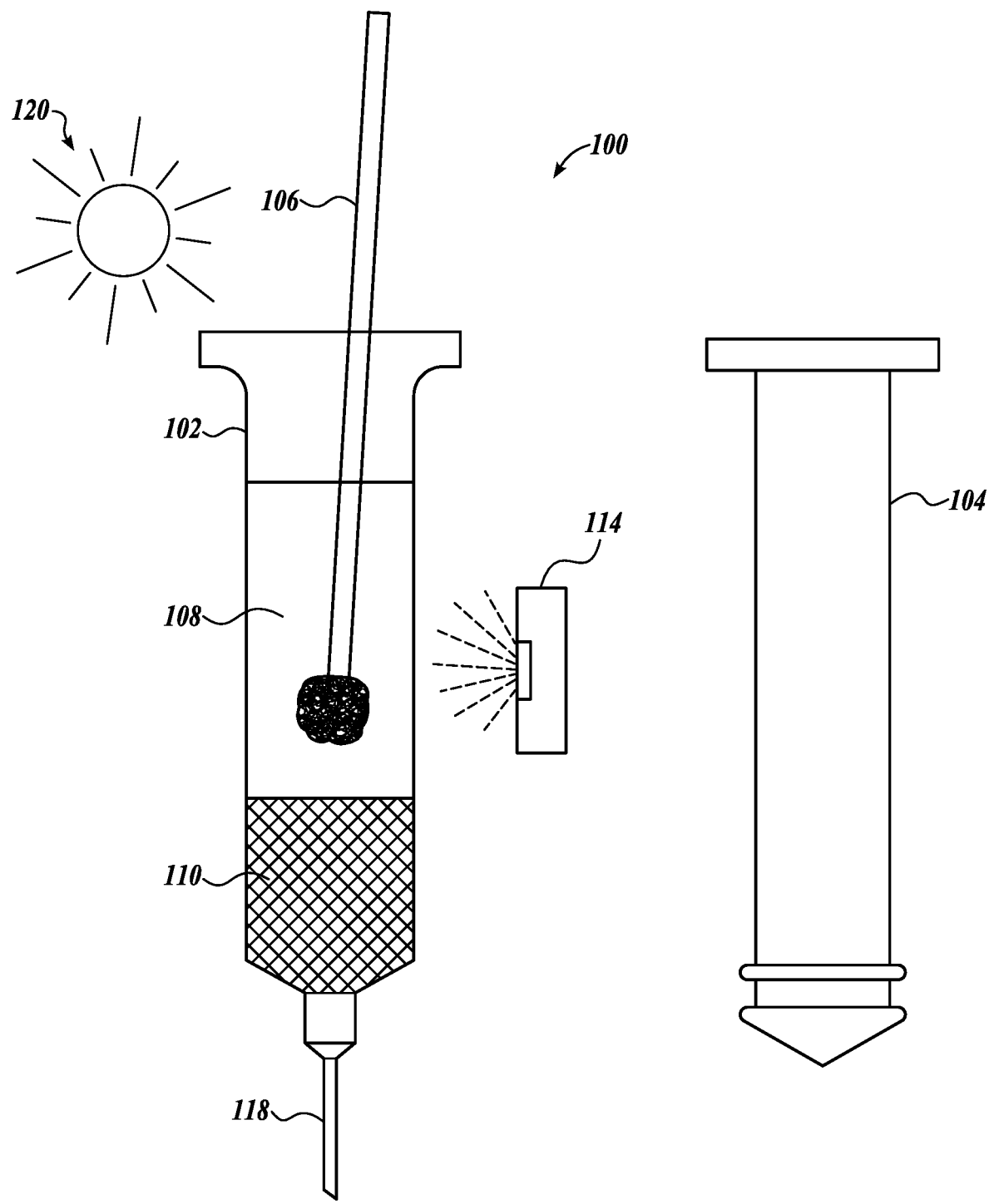
FIG. 2 is a diagrammatical illustration of an apparatus for generating a vaccine and administering the vaccine.

In another embodiment as illustrated in FIG. 2, where similar numbers represent similar parts as in FIG. 1, the filter 110 is located just proximal to the end of the cavity of the syringe 102, which then creates a reservoir containing the photodynamically treated microbial solution 108. A suitable small diameter needle 118 is attached to the syringe tip so that the vaccine solution can be inoculated intradermally, intramuscularly, or injected intravenously after passing through the filtering system 110.

It is understood that a vaccine can be generated against any type of microbial particle.

Example 1

A patient with an upper respiratory infection, for example with SARS-CoV-2, can be swabbed multiple times with multiple swabs in the mouth, nose, and nasopharynx to collect viral samples, which are then placed into the syringe 102 with the plunger 104 removed, and which has been preloaded with one or more photosensitizers in the solution 108, which could be methylene blue, for example. The swabs 106 are moved in a stirring motion with optional shaking of the syringe 102 such that microbial particles are eluted and displaced from the swabs 106 into the preloaded photosensitizer solution 108. The syringe 102 is exposed to a bright external ambient light, artificial light source 114 and/or sunlight 120 which induces a photodynamic reaction generating immunogens, such as immunogenic antigens from the inactivated, damaged microbial particles. The plunger 104 is replaced, and the solution containing immunogens is forced though a filter 110, for example a MILLIPORE® filter 110 which allows types of immunogens s to pass while trapping larger debris and unwanted microbial particles. In addition, the solution can optionally be passed through a second BLUEFLEX™ filter 116 to remove methylene blue. In one embodiment, the filtering material is incorporated into the distal end of the syringe 102 so that all of the photodynamically treated solution is forced through the filter 110 as the plunger is depressed 104.

Example 2

A patient diagnosed with a virus or pathogen can provide bodily fluid samples known to contain microbial particles, such as virus or other pathogens, in a specimen container and/or is swabbed nasally or orally to obtain virus or pathogen, which is placed into the syringe 102. If at least one swab 106 is used, the swab 106 is agitated to elute virus or other pathogen into the solution 108 containing photosensitizer, such as methylene blue. The plunger 104 is placed at the proximal end of the syringe 102 and depressed, which forces the solution 108 through a distal filter plug 110 which traps unwanted microbial particles and debris. The purified/filtered solution is a fluid that contains immunogens only, such as viral or other pathogen antigens, which are used to inoculate the patient. This purified fluid can be added to the microneedle patch 112 and administered to the patient's skin, as is done with influenza vaccine.

Example 3

The required amount and/or ratios of the one or more photosensitizers (drug dose) and a duration and waveband/wavelength of light (light dose) that is emitted at the one or more photosynthesizers can be empirically determined by generating a vaccine solution using a series of different drug doses and light doses. For example, a 1 micromolar solution is tested with a 45,000 lux light system, which produces a vaccine solution which can then be tested using preclinical testing known in the art and determined to provide maximum antigenicity, compared to lesser or greater light and/or drug doses and concentrations, and that result used to determine optimal photosensitizer and light dosing parameters.

Example 4

A patient that is diagnosed with a virus, other pathogen or toxin, can provide virally infected bodily fluids or nasal and oral swabs which are treated photodynamically and purified to generate a vaccine solution, the vaccine solution can be used to inoculate household or other contacts. The vaccine from the infected patient is used to vaccinate contacts, thus providing for an exact virus or pathogen match, in contradistinction to the yearly influenza vaccine, which is rarely or never a complete match.

Example 5

In a low resource setting, or even a military combat zone, sunlight can be used as the light source, with the sunlight dose pre-determined using solar simulator test equipment in a laboratory setting.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

As used herein and unless otherwise indicated, the terms "a" and "an" are taken to mean "one", "at least one" or "one or more". Unless otherwise required by context, singular terms used herein shall include pluralities and plural terms shall include the singular.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

All of the references cited herein are incorporated by reference. Aspects of the disclosure can be modified, if necessary, to employ the systems, functions, and concepts of the above references and application to provide yet further embodiments of the disclosure. These and other changes can be made to the disclosure in light of the detailed description.

Specific elements of any foregoing embodiments can be combined or substituted for elements in other embodiments. Moreover, the inclusion of specific elements in at least some of these embodiments may be optional, wherein further embodiments may include one or more embodiments that specifically exclude one or more of these specific elements. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

While illustrative embodiments have been illustrated and described, it will be appreciated that various changes can be made therein without departing from the spirit and scope of the invention.

The embodiments of the invention in which an exclusive property or privilege is claimed are defined as follows:

1. An apparatus for vaccine generation, comprising:
   a syringe defining a cavity for containing a solution that includes one or more photo sensitizers;
   one or more light sources capable of emitting light at one or more wavebands that activate the one or more photosensitizers to generate singlet oxygen in the solution, wherein a plurality of immunogens are created in the solution by interaction of the singlet oxygen with a plurality of microbial particles that are added to the solution, wherein the one or more light sources are configured to expose the one or more photosensitizers in the solution in the cavity of the syringe for a period of time long enough to generate the singlet oxygen that causes inactivation of the microbial particles and generation of the immunogens;
   a plunger that fits within an opening at a proximal end of the syringe, wherein advancement of the plunger from the proximal end to another position at the distal end of the syringe causes evacuation of the solution with the plurality of the immunogens through the other opening at the distal end, the plunger is removable from the syringe to introduce the solution; and
   one or more filters capable of trapping one or more of debris and the plurality of microbial particles during evacuation of the solution, wherein the one or more filters are positioned within one or more internal portions of the cavity.

2. The apparatus of claim 1, wherein the one or more photosensitizers includes one or more of erythrosine, riboflavin, or methylene blue.

3. The apparatus of claim 1, wherein the solution includes one or more aqueous solutions.

4. The apparatus of claim 1, wherein the one or more filters include a pore size from 0.1 μm to 1.0 μm.

5. The apparatus of claim 1, wherein the one or more filters, further comprise enabling removal of the one or more photosensitizers from the evacuated solution.

6. The apparatus of claim 1, further comprising a microneedle patch to which the photodynamically treated solution is applied.

7. The apparatus of claim 1, further comprising a needle that is capable of attaching to an external outlet for the other opening at the distal end of the syringe, wherein the needle is capable of delivering the evacuated solution for one or more of an intradermal, intramuscular, or intravenous injection into a user.

8. The apparatus of claim 1, wherein the cavity of the syringe further comprises a transparent material or a translucent material that is made from plastic, glass or polymer.

9. The apparatus of claim 1, wherein the one or more light sources are disposed inside the cavity of the syringe, external to the cavity of the syringe, or incorporated into a wall of the cavity of the syringe.

10. A method for vaccine generation, comprising:
    providing a solution that includes one or more photosensitizers into a syringe that defines a cavity for containing the solution;
    adding a plurality of microbial particles to the solution;
    employing one or more light sources to emit light at one or more wavebands that activate the one or more photosensitizers to generate singlet oxygen in the solution, wherein one or more types of immunogens are created by the singlet oxygen interacting with the plurality of microbial particles in the solution;
    after light exposure of the one or more photosensitizers in the solution in the cavity of the syringe for a period of time long enough to generate singlet oxygen that causes inactivation of the microbial particles and generation of immunogens, advancing a plunger that fits within an opening at a proximal end of the syringe towards a distal end of the syringe to cause evacuation of the solution with the plurality of immunogens through another opening at the distal end; and
    employing one or more filters to trap one or more of debris or the plurality of microbial particles during evacuation of the solution from the syringe, wherein the one or more filters are positioned within one or more internal portions of the cavity.

11. A method for generating a vaccine, comprising:
    filling a syringe that defines a cavity with a solution including one or more photo sensitizers;
    adding a plurality of microbial particles to the solution in the syringe;
    exposing the solution to light while inside the cavity of the syringe, wherein the light is effectively absorbed by the one or more photosensitizers to generate singlet oxygen in the solution, wherein the singlet oxygen inactivates the plurality of microbial particles and produce a plurality of immunogens in the solution; and
    after light exposure of the one or more photosensitizers in the solution in the cavity of the syringe for a period of time long enough to generate singlet oxygen that causes inactivation of the microbial particles and generation of immunogens, pressing a plunger within the cavity of the syringe to force the solution through one or more filters to produce a fluid containing the plurality of immunogens for use as a vaccine, wherein the one or more filters are positioned within one or more internal portions of the cavity.

12. The method of claim 11, wherein the plurality of microbial particles include one or more a virus, viroid, bacteria, archaea, protist, protozoa, prion, fungus, or toxin.

13. The method of claim 11, wherein the light exposes the solution to one or more of sunlight, ambient light, or artificial light at one or more wavebands or wavelengths of light that are effectively absorbed by the one or more photosensitizers to generate the singlet oxygen.

14. The method of claim 11, wherein the one or more photosensitizers further comprise methylene blue derivatives, methylene blue, chlorophyll derivatives, tetrapyrrole structures, porphyrins, chlorins, bacteriochlorins, phthalocyanines, texaphyrins, prodrugs, aminolevulinic acids, phenothiaziniums, squaraine, boron compounds, transition metal complexes, hypericin, riboflavin, curcumin, psoralens, tetracyclines, flavins, riboflavin, or titanium dioxide.

15. The method of claim 11, further comprising applying the fluid containing the plurality of immunogens to a microneedle patch.

16. The method of claim 11, wherein the syringe further comprises locating the one or more filters proximal to an end of the syringe, wherein a needle is attached to a syringe tip for intradermal, intramuscular, or intravenous injection of the fluid into a patient.

17. The method of claim 11, further comprising filtering the one or more photosensitizers from the fluid.

18. The method of claim 11, further comprising filtering one or more of debris or the plurality of microbial particles from the fluid.

19. The method of claim 11, further comprising collecting a sample of the plurality of microbial particles from a patient and transferring the sample to the cavity of the syringe.

20. The method of claim 11, comprising a filter that removes the one or more photosensitizers.

* * * * *